(12) United States Patent
Rohling et al.

(10) Patent No.: US 6,611,702 B2
(45) Date of Patent: Aug. 26, 2003

(54) APPARATUS FOR USE IN NEONATAL MAGNETIC RESONANCE IMAGING

(75) Inventors: Kenneth William Rohling, Burnt Hills, NY (US); Ronald Dean Watkins, Niskayuna, NY (US); Charles Lucian Dumoulin, Ballston Lake, NY (US); Joseph Edward Piel, Jr., Scotia, NY (US); Charles John Rossi, Jr., Amsterdam, NY (US); Randy Otto John Giaquinto, Burnt Hills, NY (US)

(73) Assignee: General Electric Company, Niskayuna, NY (US)

( * ) Notice: Subject to any disclaimer, the term of this patent is extended or adjusted under 35 U.S.C. 154(b) by 32 days.

(21) Appl. No.: 09/681,687

(22) Filed: May 21, 2001

(65) Prior Publication Data

US 2002/0173717 A1 Nov. 21, 2002

(51) Int. Cl.[7] .............................................. A61B 5/055
(52) U.S. Cl. ........................ 600/415; 600/22; 600/422; 600/411
(58) Field of Search ................................ 600/415, 407, 600/410, 22, 422

(56) References Cited

U.S. PATENT DOCUMENTS

| | | | | |
|---|---|---|---|---|
| 5,197,474 A | * | 3/1993 | Englund et al. ......... 128/653.5 |
| 5,525,905 A | * | 6/1996 | Mohapatra et al. .......... 324/318 |
| 5,619,996 A | * | 4/1997 | Beresten ................... 128/653.6 |
| 5,800,335 A | * | 9/1998 | Koch et al. .................... 600/22 |
| 5,823,960 A | * | 10/1998 | Young et al. ................ 600/415 |
| 5,990,681 A | * | 11/1999 | Richard et al. ............. 324/318 |
| 6,366,798 B2 | * | 4/2002 | Green ......................... 600/411 |

FOREIGN PATENT DOCUMENTS

| WO | 9848756 | 1/1998 | | |
|---|---|---|---|---|
| WO | WO 98/48756 A1 | * | 11/1998 | ........... A61G/11/00 |

OTHER PUBLICATIONS

WO 98/48756 A1 International Application published under the PCT, Nordell et al, "Incubator Arrangement For Use In Magnetic Resonance Imaging".*

* cited by examiner

Primary Examiner—Devaang Shah
(74) Attorney, Agent, or Firm—Jean K. Testa; Patrick K. Patnode (57) ABSTRACT

An incubator arrangement and radiofrequency (RF) coil are provided for use in a Magnetic Resonance Imaging (MRI) system. The incubator arrangement comprises an enclosure adapted to support a subject in a magnet of the MRI system during imaging and a radiofrequency coil disposed within the enclosure. The RF coil is adapted to provide visual and physical access to the subject, and further adapted to obtain a selected signal to noise ratio.

6 Claims, 8 Drawing Sheets

APPARATUS FOR USE IN NEONATAL MAGNETIC RESONANCE IMAGING

BACKGROUND OF INVENTION

This invention relates generally to medical imaging. More particularly, this invention relates to an apparatus for imaging a newborn infant who requires care in an incubator or similar life-support arrangement.

A newborn infant requiring care in an incubator has typically been born prematurely or otherwise has multiple medical needs. A typical incubator is adapted to maintain temperature, humidity and other environment aspects. Also, the incubator is typically adapted to allow various life-support mechanisms such as oxygen, intravenous medication lines, and the like to the infant, and vital signs monitoring such as echo cardiograms (EKG), blood gas, and the like. Generally, there are some significant logistical challenges in the medical imaging of newborn infants or neonates who require care in incubators. Transporting an infant from a Neonatal Intensive Care Unit (NICU) to the medical imaging area of a medical center or hospital generally requires that the infant be removed from his/her incubator at some point during the transport process, either to an intermediate transportable incubator or to the medical imaging apparatus. Further during imaging, the infant must be maintained in a similar environment (temperature, humidity, and the like) along with the required life-support mechanisms for the duration of the imaging session, which typically lasts more than one hour.

Additionally, when the medical imaging is Magnetic Resonance Imaging (MRI), there are challenges in imaging small subjects that affect the signal to noise ratio (SNR) and ultimately the image quality. Generally, neonatal imaging has been performed with RF coils used in adult head imaging. MRI radiofrequency (RF) coils, especially those of the birdcage configuration, are generally designed to optimize the signal to noise ratio for a particular application. Considerations such as the size of the subject, support mechanisms for the subject and objects that are temporarily affixed to the patient (i.e. life support, respirators, intravenous lines) generally affect the diameter of a RF coil since the above pass through the opening of the coil. The diameter of the coil has generally been increased to accommodate the above objects. An increased coil diameter has a negative effect on the signal to noise ratio—the smaller the coil diameter, the higher the SNR.

There is a need for an incubator arrangement adapted for imaging an infant requiring life-support mechanisms. Also, there is a need for a radiofrequency coil arrangement for imaging small subjects, such as an infant.

SUMMARY OF INVENTION

In a first aspect of the present invention, an incubator arrangement is provided for use in a Magnetic Resonance Imaging (MRI) system. The incubator arrangement comprises an enclosure adapted to support a subject in a magnet of the MRI system during imaging and a radiofrequency (RF) coil disposed within the enclosure. The RF coil is adapted to provide visual and physical access to the subject, and further adapted to obtain a selected signal to noise ratio.

In a second aspect, a radiofrequency (RF) coil assembly for use in MRI systems is provided. The RF coil comprises a pair of end ring conductors opposed to one another in a spaced-apart relationship and joined by a plurality of rungs. The rungs are disposed equally spaced about the end ring conductors and the rungs are configured to be recessed inward from an outer diameter defined by the respective end ring conductors.

BRIEF DESCRIPTION OF DRAWINGS

The features and advantages of the present invention will become apparent from the following detailed description of the invention when read with the accompanying drawings in which.

DETAILED DESCRIPTION

Figure 1:
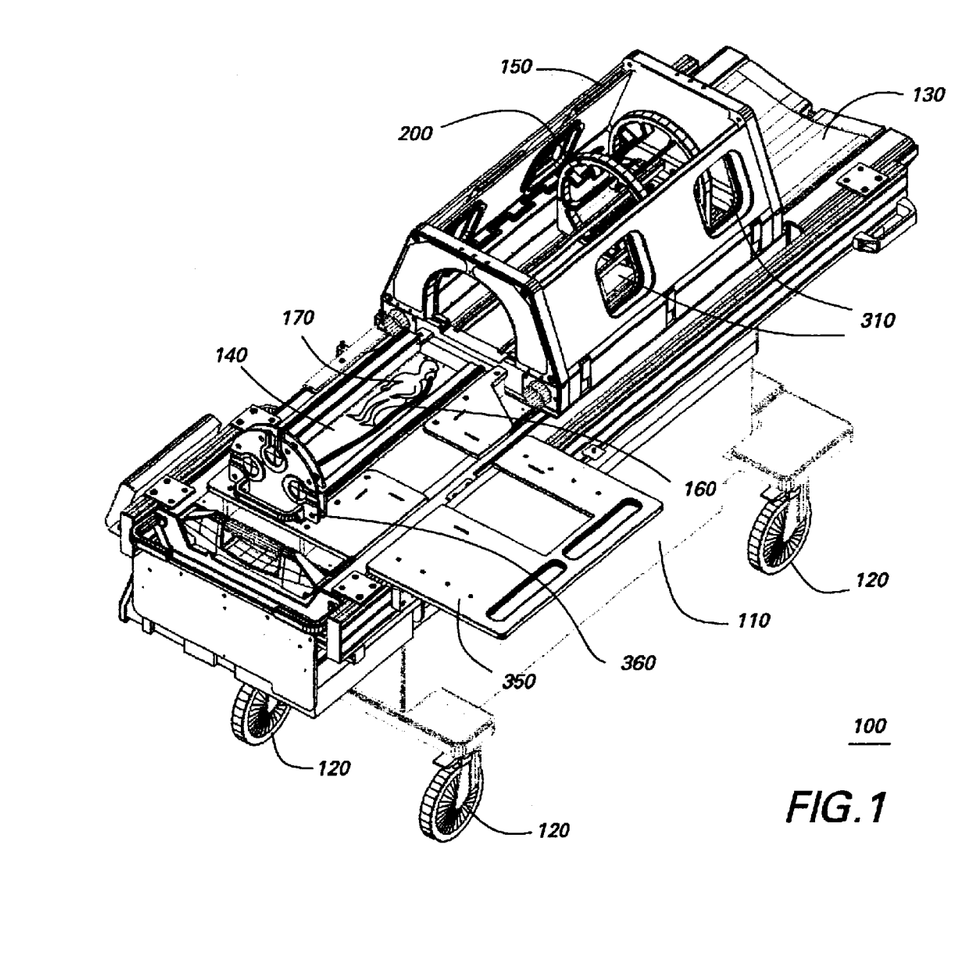
FIGS. 1 and 2 are illustrations of an exemplary incubator arrangement to which preferred embodiments of the present invention are applicable.

FIG. 1 illustrates an exemplary incubator arrangement 100 to which preferred embodiments of the present invention are applicable for use in a Magnetic Resonance Imaging (MRI) system, such as the GE 1.5 T SIGNA magnet which is a closed, cylindrical magnet. Although the present invention is described in connection with a cylindrical, closed magnet, it is to be appreciated by those skilled in the art that the embodiments of the present invention are adaptable and applicable to open MRI systems.

Referring to FIG. 1, incubator arrangement 100 comprises a base unit 110, wheels 120, a support table 130, a subject carrier unit 140, an enclosure 150, life support mechanisms 160 and a radiofrequency (RF) coil 200. Incubator arrangement 100 is desirably constructed as a single unit including, in particular, the components above so that incubator arrangement 100 is adapted to substantially minimize the logistics of transferring an infant from a NICU incubator to be imaged with a MRI system. It is to be appreciated that an integrated and self-contained incubator arrangement as described herein avoids unnecessary transfer of a separate incubator and associated equipment during an imaging procedure. Incubator arrangement is described herein for use in imaging, however it may be used for short-term use and, alternatively, long-term care of the infant patient. Incubator arrangement 100 includes base 110 and wheels 120 for transportation purposes. Base 110 is adapted to accommodate air and oxygen units, intravenous equipment, physiological monitoring equipment, a portable power source or battery pack and other similar equipment and supplies for use in transporting a subject 170. As used herein, "adapted to", "configured" and the like refer to mechanical or structural connections between elements to allow the elements to cooperate to provide a described effect; these terms also refer to operation capabilities of electrical elements such as analog or digital computers or application specific devices (such as an application specific integrated circuit (ASIC)) that are programmed to perform a sequel to provide an output in response to given input signals.

Support table 130 is mounted on base unit 110. Support table 130 is adapted to connect with the MRI system such that support table 130, subject carrier 140, enclosure 150, life support mechanisms 160 and RF coil 200 are movable along a displacement axis, typically a longitudinal axis, in relation to the magnet bore of the MRI system. Incubator arrangement 100 further includes cable connections (not shown) for connection to the MRI system, table displacement controls and other physiological monitoring equipment. Incubator arrangement 100 desirably also includes cables and hoses that can be attached to hospital infrastructure for extended use of electrical power and/or gases.

Incubator arrangement 100 is desirably used in place of the patient table of a conventional MRI system. A patient table is typically used in MRI systems to move a subject into the imaging space of the MRI system. In embodiments of the present invention, the patient table of a conventional MRI system is desirably removed and incubator arrangement 100 is used in its place. In a typical MRI system, the imaging space is defined by the inner diameter of the magnet bore and is sufficiently large enough, typically about 55 to about 60 cm, to accommodate a subject or a portion of a subject. In embodiments of the present invention, the dimension of support table 130, subject carrier unit 140 and enclosure 150 in combination is selected so that they are accommodated by the imaging space and further permit longitudinal translation into the magnet bore. Additionally, support table 130, subject carrier 140, enclosure 150, life support mechanisms 160 and RF coil 200 are of materials and construction able to withstand very strong magnetic fields of about 1.5 Tesla (1.5 T) or greater. It is to be appreciated by those skilled in the art that the embodiments of the present invention are also applicable to MRI systems employing magnetic fields exceeding 1.5 T, such as 3 T and greater.

Subject carrier unit 140 supports subject 170, generally an infant in a lying down position. Subject carrier unit 140 and enclosure 150 are disposed and mounted on support table 130. RF coil 200 is disposed within enclosure 150. Subject carrier 140 is desirably movable in relation to enclosure 150 and RF coil 200, and is desirably mounted on support table to permit moving subject carrier 140, such as by longitudinal translation or sliding, to be disposed within RF coil 200 which is disposed within enclosure 150. Enclosure 150 is desirably adapted to maintain an environment prescribed for neonates. Aspects of enclosure 150 will be further discussed with reference to FIG. 2. In order to position subject 170 into the MRI system, subject carrier unit 140 is moved within enclosure 150 and is adapted to be disposed within an inner diameter of RF coil 200. Aspects of RF coils 200 will be further discussed with reference to FIGS. 3 and 4. Referring further to FIG. 1, support table 130 is adapted to displace subject 170, once positioned within enclosure 150 and RF coil 200, into the imaging space of the MRI system. The position of RF coil 200 relative to subject 170 is adjustable so that RF coil 200 is positioned along selected longitudinal sections of subject's body.

Typically, life support mechanisms for neonates require substantially constant operation and must remain connected to the infant during the imaging session. Life support mechanisms 160 refer generally to air and oxygen tubes, respirators, intravenous tubes and catheters to supply fluids and medications to the subject 170 and also to physiological sensors to be connected from the subject to physiological monitoring equipment. Life support mechanisms 160 are desirably adapted for use in magnetic fields and are selected from generally non-magnetic materials. Incubator arrangement 100 is adapted to maintain substantially constant operation of life support mechanisms 160 during imaging. In the present invention, subject 170 is desirably placed in subject carrier unit 140 while maintaining various connections to life support mechanisms. Further, subject carrier unit 140 and enclosure 150 are adapted to enable the various connections to subject 170. Alternatively, subject carrier unit 140 and enclosure 150 are adapted such that connections to various life support mechanisms is made substantially immediately after placing subject 170 onto subject carrier unit 140.

Figure 2:
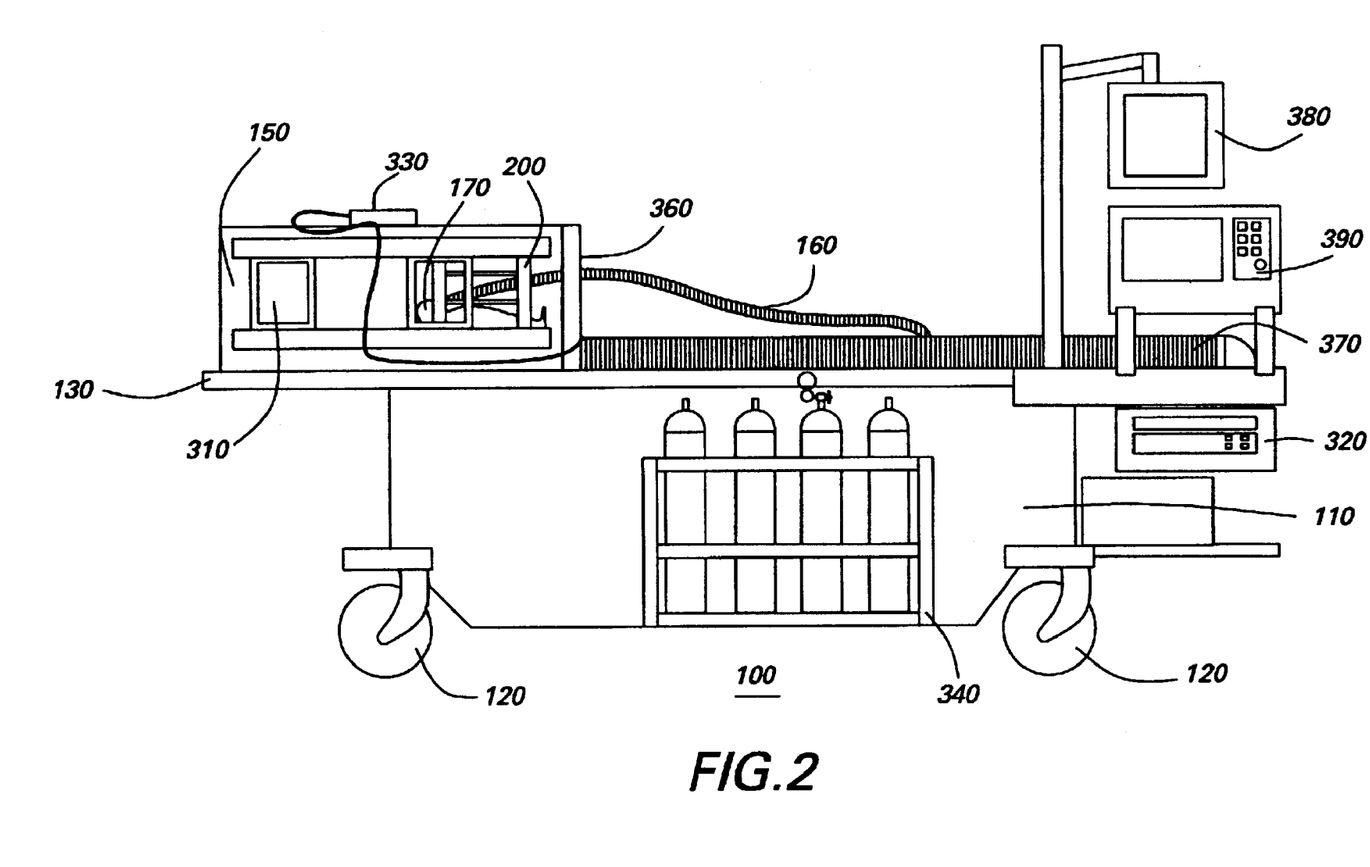

FIG. 2 illustrates additional aspects of incubator arrangement 100 and enclosure 150. In alternative embodiments of incubator arrangement 100, additional features are provided, as shown in FIG. 2, to further enable the care and transport of a neonate. Enclosure 150 is desirably constructed of transparent material and also is constructed as a double walled structure adapted for thermal and acoustic insulation. Enclosure 150 is further equipped with one or more sliding access panels 310 to permit access to the infant. In a further embodiment, incubator arrangement 100 includes a video camera 330, or alternatively other visual monitoring devices, for visually monitoring the infant when he/she is positioned in enclosure 150. In another further embodiment, incubator arrangement 100 comprises environment controller 320 for maintaining temperature and/or gas levels. Further, incubator arrangement 100 is adapted to include a plurality of gas cylinders and enclosure 340, for example attached to base unit 110 adapted to store the cylinders, that are transportable with the infant. Referring to FIG. 1, in another further embodiment, incubator arrangement 100 further comprises a transfer table 350 adapted to transfer the infant from a NICU incubator to incubator arrangement 100. Transfer table 350 is desirably attached to base unit 110 of incubator arrangement 100; transfer table 350 does not travel into the magnet and is desirably adapted to fold down adjacent to base unit 110 when not in use. Also referring to FIG. 1, incubator arrangement 100 further comprises an enclosure sealing unit 360 adapted to seal the environment within enclosure 150 as well as sealing unit 360 is adapted to allow passage of connections to various life support mechanisms 160.

Referring further to FIG. 2, incubator arrangement 100 further includes a heater tube assembly 370, which will be described in greater detail below with reference to FIG. 8, a display 380 and a monitor display 390. Heater tube assembly 370 is adapted to deliver the required air at a selected temperature to the environment of incubator arrangement 100. Heater tube 370 is coupled to enclosure 150 and is further adapted to extend and collapse as enclosure 150 is translated along the displacement axis into the magnet of the MRI system. Display 380 is coupled to video camera 330 so that a technician or physician may have visual access to the infant. Monitor display 390 is coupled to physiological monitors attached to the infant to monitor various vital signs.

Figure 3:
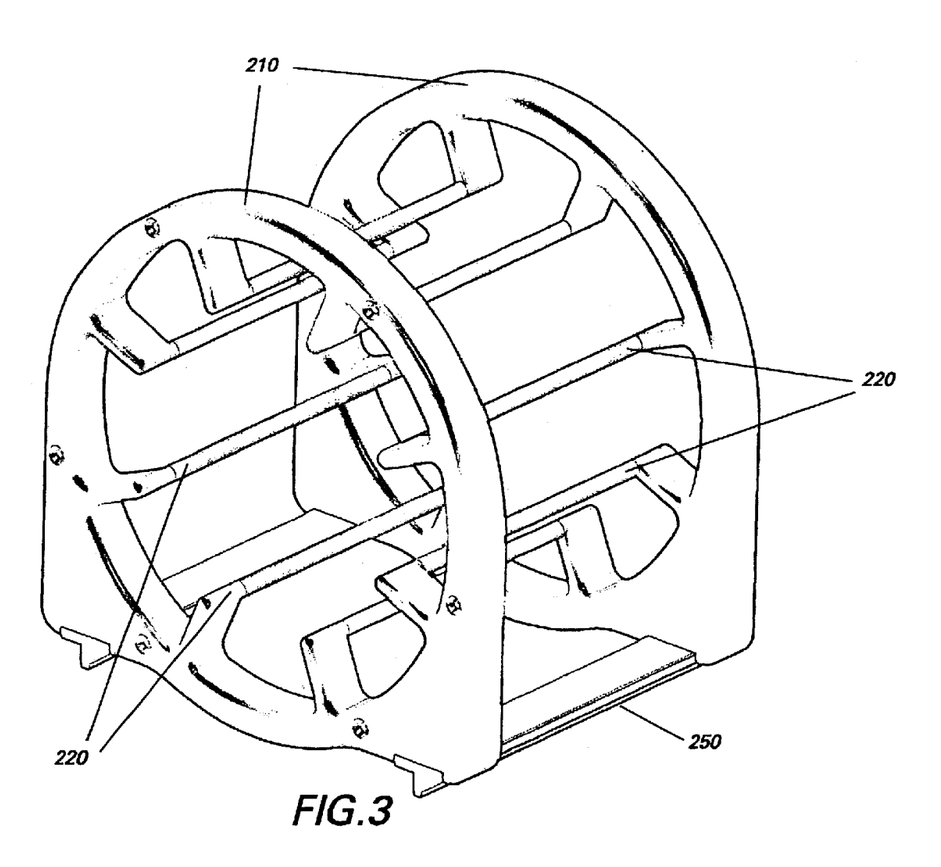
FIGS. 3 and 4 are respective views of an embodiment of a radiofrequency coil (RF) useful in the incubator arrangement of FIGS. 1 and 2.
Figure 4:
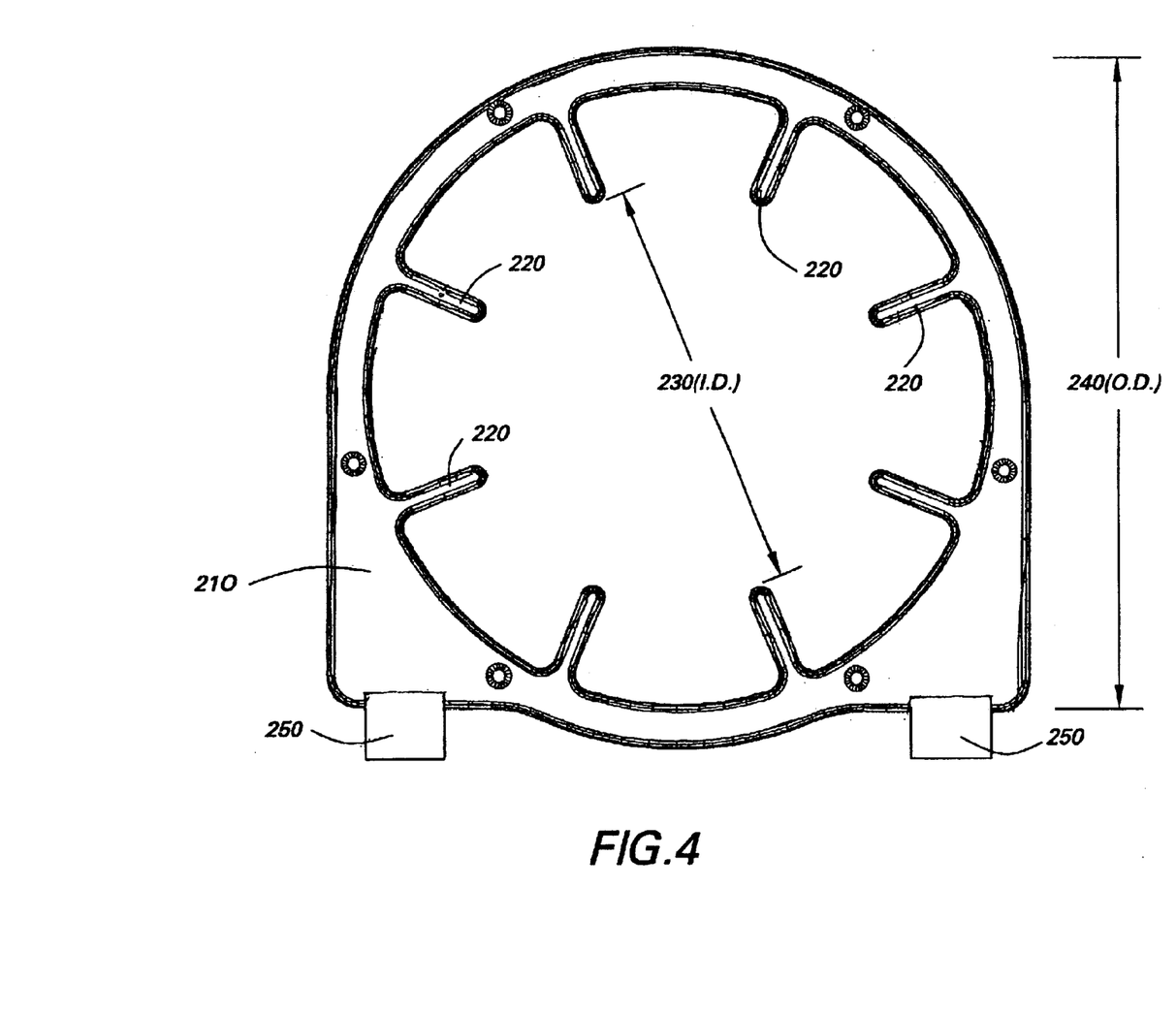

FIGS. 3 and 4 illustrate an exemplary embodiment of RF coil 200 to which embodiments of the present invention are applicable for use in a MRI system. FIG. 3 is side view of RF coil 200. Referring to FIG. 3, RF coil 200 is configured as a birdcage coil, modified according to embodiments discussed below, comprising two end ring conductors 210 and a plurality of rungs 220. End ring conductors 210 oppose one another in a spaced-apart relationship and are joined together by a plurality of rungs 220 disposed between and connecting end ring conductors 210. End ring conductors 210 are desirably circular, but it is to be appreciated that other configurations, such as elliptical or oval, may alternatively be used. The distance or space between end ring conductors is selected for the particular imaging application. For example, for the embodiment of FIG. 1, the distance must be sufficiently large enough to accommodate subject carrier unit 140. The outer dimension of RF coil 200 is selected to fit within enclosure 150. A plurality of rungs 220 are disposed in equally spaced intervals about the circumference of end ring conductors 210. Each of rungs 220 is an inductive element. In conventional birdcage RF coils, rungs are placed at a radial distance substantially equal to the radius of the end rings.

End ring conductors 210 and rungs 220 form a resonant structure, also known as a MR imaging coil. The resonant structure can operate as a transmit or receive coil in the MRI system. The resonant structure can be supplied with RF energy for the purpose of nutating longitudinal MR magnetization into the transverse plane. Alternatively, the resonant structure can be used to detect the MR signal which can then be used to reconstruct an image of an area of interest within the subject, in a manner well known to those skilled in the art. Further included in RF coil 200 is a mounting device 250 for mounting RF coil within incubator arrangement 100 (FIG. 1). As described above, the position of RF coil 200 within enclosure 150 (FIG. 1) of incubator arrangement 100 is desirably adjustable to image selected sections of the subject. Mounting device 250 is adapted to secure RF coil 200 within incubator arrangement 100 once the position of RF coil 200 is selected. Mounting device 250 is shown in FIGS. 3 and 4 as an integrated part of RF coil 200 forming a single unit, achievable by machining, for example. In an alternative embodiment, mounting device 250 is at least one separate device similarly adapted to secure RF coil 200 within incubator arrangement 100.

RF coil 200 is constructed of materials well known in the field of RF coil technology for MRI systems and is desirably comprised of non-magnetic materials. Examples of suitable materials for constructing RF coil 200 include copper and/or silver for electrical conductors, ceramic chip capacitors and fiberglass and epoxy resins for structural members.

Figure 5:
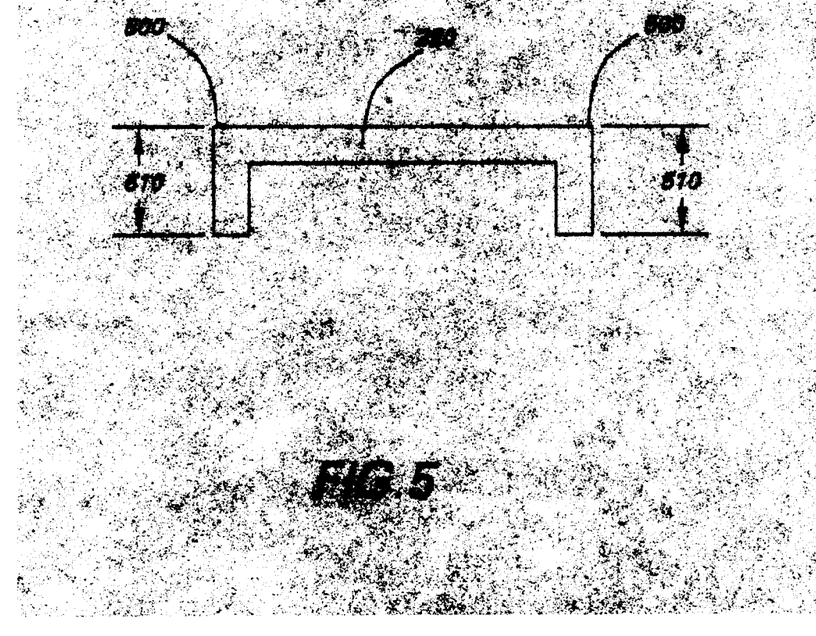
FIG. 5 is an illustration of an exemplary embodiment of rungs useful in the RF coil of FIGS. 3 and 4.

Referring to FIG. 4, an end view of RF coil 200, rungs 220 are recessed inward from the outer diameter formed by end ring conductors 210. As used herein, the term recessed refers generally to displacement along a straight line from a point or surface. In this embodiment of RF coil 200, rungs 220 are displaced inwardly a selected distance from the surface of the inner diameter of end ring conductors 210, as shown in FIG. 4. Rungs 220 are desirably configured as shown in FIG. 5, in which respective ends of each rung 220 are desirably bent at bends 500 to a ninety-degree angle to effect the recessed condition described above. Other configurations, such as curves or angles less than ninety-degrees, that effect the recessed condition are alternative embodiments. Between bend 500 and each respective end of rungs 220 is a recess distance 510. Recess distance 510 is selected to effect the desired inner diameter 230 dimension of RF coil 200 used in MR imaging. Each of rungs 220 is similarly configured to be substantially identical. RF coil 200 comprises a plurality of similarly configured rungs. In an embodiment, 8 rungs are employed. It is to be appreciated that more or fewer rungs, generally an even number and factor of 4, may be alternatively used depending on the desired MR imaging application and constraints that are well known to one skilled in the art. The number of rungs 200 is desirably 8 for neonatal imaging to provide sufficient resonance during the MRI scanning as well as to provide physical spacing between rungs to allow physical and visual access to the subject or infant. In an exemplary embodiment for neonatal imaging using a MRI system, outer diameter 240 of RF coil 200 is desirably between a range of about 27 cm and about 31 cm, such that RF coil is accommodated by enclosure 150 of FIG. 1. Also in this exemplary embodiment, inner diameter 230 of RF coil 200 is desirably between a range of about 16 cm and about 17 cm, and preferably in the range of about 16.4 cm and about 16.8 cm.

Figure 6:
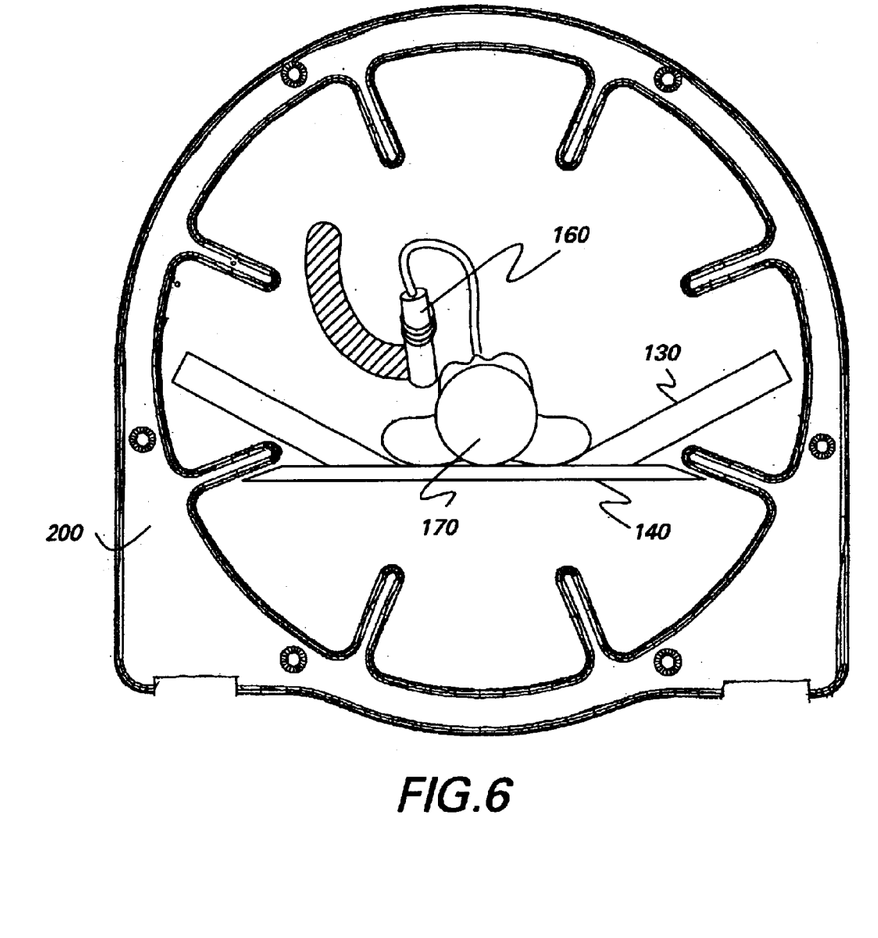
FIG. 6 is an illustration of embodiments of a radiofrequency coil and a subject carrier unit useful in the incubator arrangement of FIGS. 1 and 2.

Inner diameter 230 of RF coil 200 is configured to allow passage of subject 170 (FIG. 1), various life support mechanisms 160 (FIG. 1) and subject carrier unit 140 (FIG. 1) into the imaging space of the MRI system while maintaining desirable signal to noise ratios (SNR), typically greater than or equal to 30. Referring to FIG. 6, there is shown a close-up view of subject 170 lying on subject carrier unit 140 and positioned within RF coil 200.

Further, incubator arrangement 100 comprises various electronics housed in base unit 110 (FIG. 1) and desirably base unit 110 is adapted to house the electronics in a Faraday cage arrangement, such as copper lined chambers filtering capacitors coupled to the chamber walls too attenuate RF noise emissions on every lead entering and exiting the Faraday cage. Further, incubator arrangement 100 includes a balun arrangement (not shown) adapted to operate with RF coil 200, as configured in embodiments of the present invention.

Figure 7:
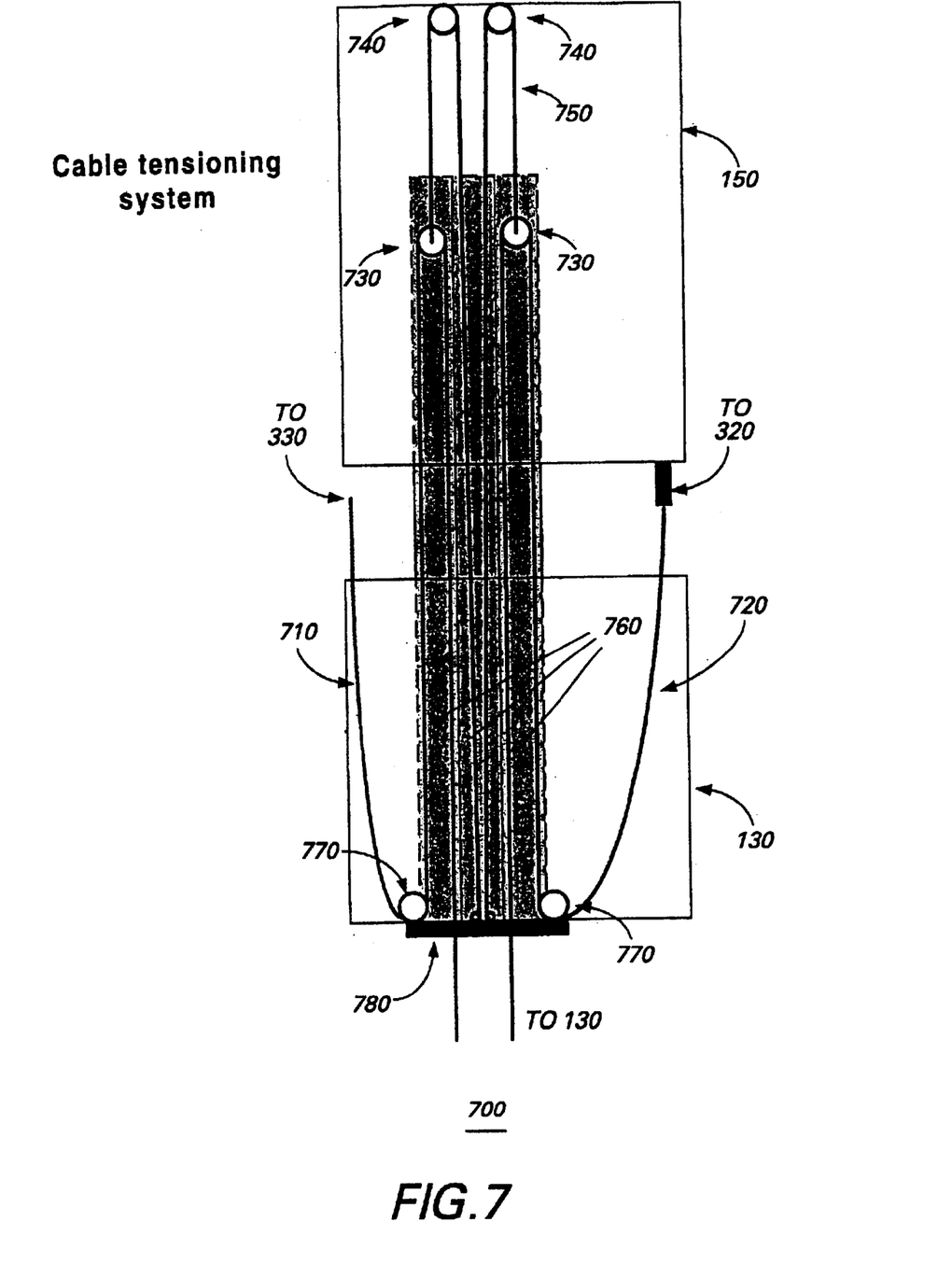
FIG. 7 is an illustration of a cable take-up assembly for use in the incubator arrangement of FIGS. 1 and 2; and, FIG. 8 is an illustration of a heater tube assembly for use in the incubator arrangement of FIGS. 1 and 2.

FIG. 7 illustrates a cable take up assembly 700 useful in embodiments of incubator arrangement 100 (FIG. 1). Cable take up assembly 700 is positioned out of view and generally under enclosure 150 of FIG. 1. Cable take up assembly is adapted to store and permit movement of cables that feed from enclosure 150 of FIG. 1 as enclosure 150 translates along the displacement axis of the MRI system. In an exemplary embodiment, cables such as video camera cable 710 that connects to video camera 330 (FIG. 1) and temperature sensor cable 720 that connects to environment controller 320 (FIG. 1) are attached in an arrangement as shown in FIG. 7. In this embodiment, cables 710 and 720 are each attached to a plurality of pulleys 730 and 740 coupled to flexible cord 750 to create a tensioning system for cables 710 and 720. Further, channels 760 are provided to guide the cables. Strain relief devices 770 are provided. The length of channels 760, flexible cord 750 and cables 710 and 720 are each selected to permit translation of enclosure 150 into the magnet. An arrangement according to this embodiment permits extension of the cables when enclosure 150 is translated into the magnet of the MRI system and further permits retraction and storage of the cables when enclosure 150 exits from the magnet. Cable take up assembly 700 further comprises a roller 780 to secure each of the cables in a guided relationship with channels 760, and roller 780 is further adapted to prevent the cables from tangling within the assembly 700. Cable take up assembly 700 is constructed of materials that are compatible with MRI systems, and are preferably of non-magnetic materials. Further, pulleys 730 and 740, strain reliefs 770 and channels 760 are constructed of materials that minimize and substantially prevent wear of the various cables. In the present embodiment, cable take up assembly 700 is adapted to accommodate video and thermal sensor cables. Alternatively, cable take up assembly 700 accommodates fiber optic, EKG, EEG (electroencephalogram), blood gas, blood pressure and other physiological or environmental cables in a manner described herein.

Figure 8:
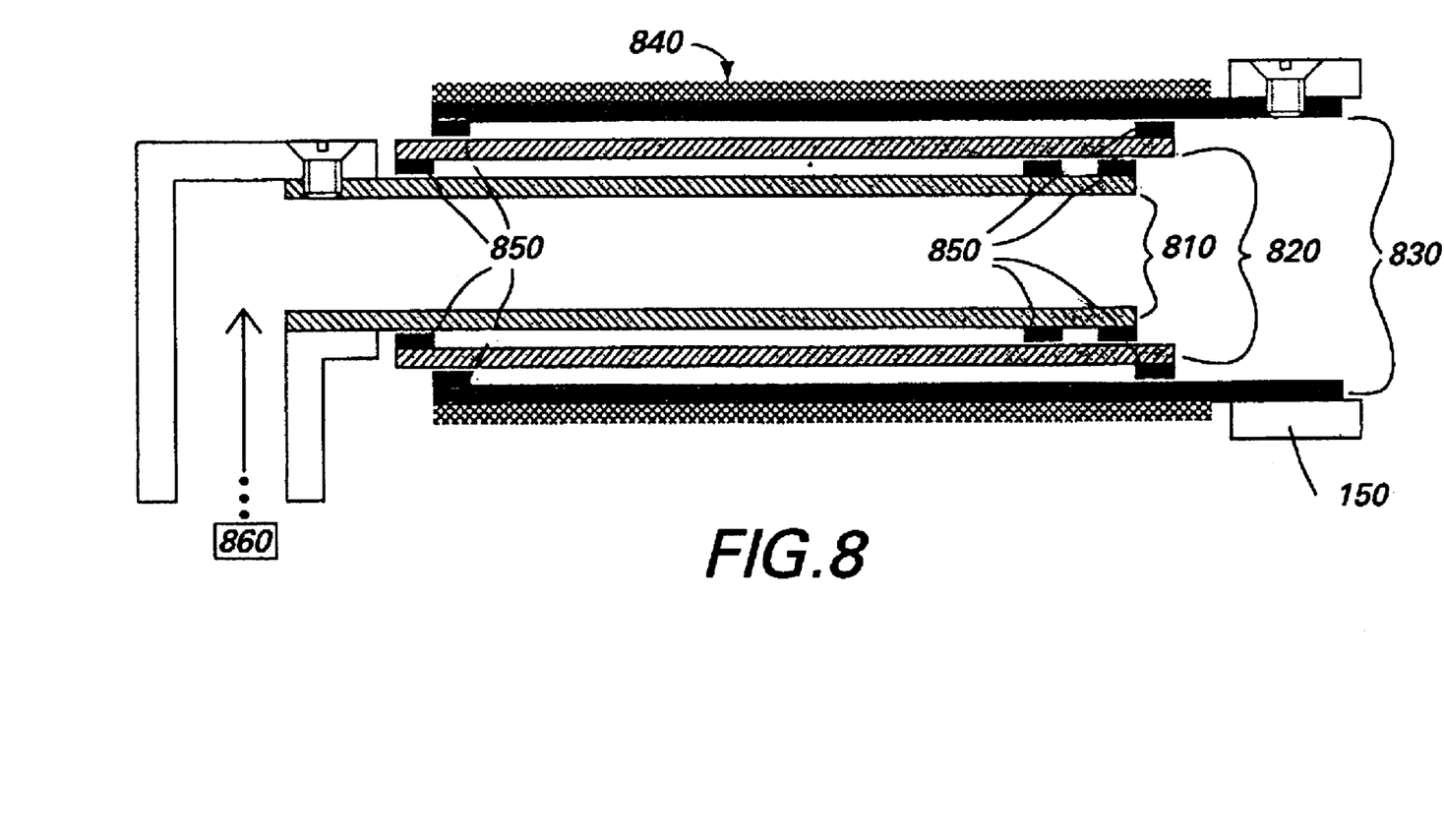

FIG. 8 illustrates a cross-sectional view of an embodiment of a heater tube assembly useful in embodiments of incubator arrangement 100 of FIGS. 1 and 2. Heater tube assembly 800 is adapted to transfer temperature controlled air from a heater 860 to enclosure 150 in a manner described herein. Heater tube assembly 800 comprises inner tube 810 disposed within middle tube 820 which is disposed within outer tube 830. Tubes 810, 820 and 830 are desirably constructed of polycarbonate tubing, or other similar non-magnetic material. Inner tube 810 is fixably and rigidly attached to heater 860. Outer tube 830 is fixably and rigidly attached to enclosure 150 and support table 130 (shown in FIG. 1). Outer tube 830 is desirably covered with insulator 840. Insulator 840 is desirably a rugged ribbed cover. Gaskets 850 are disposed at respective ends and between respective tubes 810, 820 and 830 to hold the tubes in place relative to one another while permitting movement of the tubes and to prevent escape of the temperature controlled air. Two gaskets 850 are placed at the enclosure end of inner tube 810 to reduce sagging when heater tube assembly 800 is fully extended as described below. In this embodiment, when enclosure 150 is translated along the displacement axis of the MRI system, tubes 810, 820, 830 and insulator 840 cooperate to extend as enclosure 150 enters the magnet of the MRI system. As enclosure 150 is displaced, outer tube 830 being attached to enclosure 150 is also displaced. Inner tube 810 being fixably attached to heater 860 remains stationary and middle tube 820 is extended between inner 810 and outer 830 tubes as enclosure 150 is displaced. Conversely, when enclosure 150 exits the magnets and translates back to a starting position in the MRI system, tubes 810, 820, 830 and insulator 840 cooperate to collapse to a starting length. In this embodiment, incubator arrangement 100 is adapted to provide temperature controlled air to enclosure 150 without extraneous heating tube devices, or without placing a heating element and/or fan assembly into the bore of the magnet.

It is to be appreciated that embodiments of RF coil 200 are applicable to MR imaging applications other than neonatal imaging. Outer and inner diameters and number of rungs are alternatively selectable depending on the imaging application. For example, body and head birdcage coil assemblies may be constructed with recessed rungs to effect a reduced inner diameter of the coil and maintain a desired signal to noise ratio.

Because of the need for patient access and the geometry of the surrounding conducting surfaces, RF coil 200 does not employ a RF shield. A conventional RF shield would prevent interactions between RF coil 200 and the surrounding magnet, as well as interfering with access to the subject. Designs in which RF shields are incorporated into the coil are possible. If used, these RF shields are desirably configured to have openings to provide access to the subject. Another embodiment of the invention comprises the incorporation of an open RF shield.

While the above embodiments have been presented in connection with neonatal imaging using a MRI system, it is to be appreciated that embodiments of incubator arrangement 100 are applicable for other medical imaging techniques, such as computed tomography (CT). It is to be further appreciated that embodiments of RF coil 200 are applicable to subjects other than small subjects or infants. For example, RF coil 200 is modifiable for body and head coil assemblies. Further, embodiments of the present invention are applicable to higher field strengths (greater than 1.5 T) and may be used in open and closed magnets of MRI systems.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. An incubator arrangement for use in a Magnetic Resonance Imaging (MRI) system:

a base;

a support table attached to said base and moveable thereon, said support able adapted to move to be disposed within an imaging space of said MRI system;

a subject support unit attached to said support table and moveable thereon, said subject support unit being adapted to support an infant;

an enclosure attached to said support table and adapted for receiving said infant on said subject support unit, said enclosure further comprising sliding access panels to provide physical access to said infant, said enclosure being adapted to maintain a selected environment and being further adapted to permit a coupling of a plurality of life support mechanisms to said infant, said enclosure further adapted to provide visual access to said subject; and, a radiofrequency (RF) coil disposed within said enclosure and adapted to receive at least a portion of said infant, said RF coil being adapted to provide visual and physical access to said infant, and being further adapted to obtain a selected signal to noise ratio.

2. The incubator arrangement of claim 1 further comprising a cable take up assembly adapted to store and permit tensioned movement of at least one cable that feeds from said enclosure to at least one of external visual and environment controls.

3. The incubator arrangement of claim 1 further comprising a heater tube assembly adapted to transfer temperature controlled air from a heater to said enclosure, said heater tube assembly comprising a plurality of tubes adapted to cooperate to extend and retract as said enclosure is translated along the displacement axis into the magnet of the MRI system.

4. The incubator arrangement of claim 1 wherein said base is further configured for attenuation of RF emissions.

5. The incubator arrangement of claim 4 wherein said base further comprises a plurality of copper lined chambers and a plurality of filtering capacitors coupling leads into and out of said chambers to said copper.

6. The incubator arrangement of claim 1 further comprising a transfer table coupled to said support table and adapted to transfer said infant onto said incubator arrangement.

\* \* \* \* \*